(12) United States Patent
Neumann

(10) Patent No.: US 11,594,317 B2
(45) Date of Patent: Feb. 28, 2023

(54) METHODS AND SYSTEMS FOR DETERMINING A PLURALITY OF NUTRITIONAL NEEDS TO GENERATE A NUTRIENT SUPPLEMENTATION PLAN USING ARTIFICIAL INTELLIGENCE

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/886,661

(22) Filed: May 28, 2020

(65) Prior Publication Data
US 2021/0375427 A1   Dec. 2, 2021

(51) Int. Cl.
*G16H 20/60*   (2018.01)
*G16H 50/20*   (2018.01)
(Continued)

(52) U.S. Cl.
CPC ........... *G16H 20/60* (2018.01); *A61B 5/4866* (2013.01); *A61B 5/7264* (2013.01);
(Continued)

(58) Field of Classification Search
CPC ........ G16H 20/60; G16H 50/50; G16H 10/60; G16H 50/30; G16H 50/20; G06N 20/00;
(Continued)

(56) References Cited

U.S. PATENT DOCUMENTS 7,136,820 B1   11/2006   Petrus
7,295,889 B2   11/2007   Lahteenmaki
(Continued)

FOREIGN PATENT DOCUMENTS

AU   2018232935   4/2019
CN   108766511   11/2018
(Continued)

OTHER PUBLICATIONS

Poslusna,K.,Ruprich, J.,deVries,J.H.,Jakubikova,M.,&van'tVeer,P. (2009). Misreportingofenergyandmicronutrientintake estimatedbyfoodrecordsand24hourrecalls,controlandadjustmentmethodsinpractice. BritishJournalofNutrition,101(S2), S$73-S85. (Year: 2009).*
(Continued)

*Primary Examiner* — Joshua B Blanchette
*Assistant Examiner* — Winston Furtado
(74) *Attorney, Agent, or Firm* — Caldwell Intellectual Property Law

(57) ABSTRACT

A system for determining a plurality of nutritional needs of a user and generating a nutrient supplementation plan using artificial intelligence includes at least a computing device designed and configured to receive, from a user, at least a biological extraction, generate, using the at least a biological extraction and a first machine-learning process, a plurality of nutritional needs of the user, determine a nutritional input to the user, detect at least a nutrition deficiency as a function of the plurality of nutritional needs and the nutritional input, and calculate at least a supplement dose from the plurality of nutritional needs and at the least a nutrition deficiency.

16 Claims, 4 Drawing Sheets

(51) Int. Cl.
*G16H 50/30* (2018.01)
*G16H 10/60* (2018.01)
*G06N 20/00* (2019.01)
*G16H 50/50* (2018.01)
*A61B 5/00* (2006.01)

(52) U.S. Cl.
CPC ........... *A61B 5/7267* (2013.01); *G06N 20/00* (2019.01); *G16H 10/60* (2018.01); *G16H 50/20* (2018.01); *G16H 50/30* (2018.01); *G16H 50/50* (2018.01)

(58) Field of Classification Search
CPC .... A61B 5/4866; A61B 5/7264; A61B 5/7267
USPC ............................................................ 705/2
See application file for complete search history.

(56) References Cited

U.S. PATENT DOCUMENTS

| | | |
|---|---|---|
| 8,968,806 B2 | 3/2015 | Delaney |
| 9,704,096 B2 | 7/2017 | Hudson et al. |
| 10,360,495 B2 | 7/2019 | Chapela et al. |
| 10,492,519 B2 | 12/2019 | Capell et al. |
| 2006/0099310 A1 | 5/2006 | Koekkoek |
| 2008/0195594 A1 | 8/2008 | Gerjets et al. |
| 2011/0014351 A1 | 1/2011 | Reider et al. |
| 2011/0054928 A1 | 3/2011 | Sullivan |
| 2015/0269865 A1 | 9/2015 | Volach |
| 2017/0249445 A1* | 8/2017 | Devries ................. G16H 20/60 |
| 2019/0031488 A1 | 1/2019 | Iotti et al. |
| 2019/0145988 A1 | 5/2019 | Haddad et al. |
| 2020/0005928 A1* | 1/2020 | Daniel .................. G16H 20/30 |
| 2021/0233615 A1* | 7/2021 | Banavar ................ G16H 50/70 |

FOREIGN PATENT DOCUMENTS

| | | | | |
|---|---|---|---|---|
| DE | 102015113942 A1 * | 2/2016 | ............ | G06F 40/56 |
| JP | 2006285967 A * | 10/2006 | ............ | G06Q 50/22 |
| KR | 20180116779 A * | 10/2018 | ............ | G06N 99/00 |
| WO | WO0039777 | 7/2000 | | |
| WO | WO2019241167 | 12/2019 | | |

OTHER PUBLICATIONS

Petot, G. J., Marling, C., & Sterling, L. (1998). An artificial intelligence system for computer-assisted menu planning. Journal of the American Dietetic Association, 98(9), 1009-1014. (Year: 1998).*
https://www.algemeiner.com/2019/12/19/israeli-company-looks-to-digitize-diet-tracking-and-vitamin-intake-with-smart-dispenser/.
https://www.teknoscienze.com/tks_article/artificial-intelligence-and-dietary-supplements-from-product-formulation-to-consumer-personalization/.
Aboelfotoh, Muhammad Hosam.Queen's University (Canada), ProQuest Dissertations Publishing, 2017. 10707049.
https://arxiv.org/abs/1803.07877v1.

* cited by examiner

METHODS AND SYSTEMS FOR DETERMINING A PLURALITY OF NUTRITIONAL NEEDS TO GENERATE A NUTRIENT SUPPLEMENTATION PLAN USING ARTIFICIAL INTELLIGENCE

FIELD OF THE INVENTION

The present invention generally relates to the field of artificial intelligence. In particular, the present invention is directed to methods and systems for determining nutritional needs to generate a nutrient supplementation plan using artificial intelligence.

BACKGROUND

Design of systems for analysis of nutritional data is often frustrated by the extreme complexity and variability of the subject matter between subjects. A vast multiplicity of factors to be considered is further complicated by a complex array of subtle, but crucial data. Worse still, a given factor may vary significantly between subjects, and in ways that can frustrate consistent application of nutritional data to analytical techniques.

SUMMARY OF THE DISCLOSURE

In an aspect, a system for determining a plurality of nutritional needs of a user and generating a nutrient supplementation plan using artificial intelligence includes at least a computing device designed and configured to receive, from a user, at least a biological extraction, generate, using the at least a biological extraction and a first machine-learning process, a plurality of nutritional needs of the user, determine a nutritional input to the user, wherein determining the nutritional input to the user comprises; receiving user-reported data describing the nutritional input; calculating a user misreporting factor; and weighting the user-reported data with the user misreporting factor; detect at least a nutrition deficiency as a function of the plurality of nutritional needs and the nutritional input, and calculate at least a supplement dose from the plurality of nutritional needs and at the least a nutrition deficiency.

In another aspect, a method of calculating at least a supplement dose using at least an element of user data and artificial intelligence, the method comprising receiving, by at least a computing device, at least an element of biological extraction data, generating, by at least a computing device, using the biological extraction data and at least a first machine-learning process, at least a nutritional need of the user, determining, by at least a computing device, a nutritional input to the user, wherein determining the nutritional input to the user comprises; receiving user-reported data describing the nutritional input; calculating a user misreporting factor; and weighting the user-reported data with the user misreporting factor, detecting, by at least a computing device, at least a nutrition deficiency as a function of at least a nutritional need and the nutritional input, and calculating, by at least a computing device, at least a supplement dose from at least a nutritional need and at the least a nutrition deficiency.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a system and method for determining a plurality of nutritional needs to generate a nutritional supplement plan using artificial intelligence. In non-limiting embodiments described herein, artificial intelligence may refer to a machine learning process, as described in further detail below. In non-limiting embodiments, system may receive at least a biological extraction, as defined below. In non-limiting embodiments, determining a plurality of nutritional needs may use biological extraction data, as described in further detail below. Biological extraction data may be used as an input to at least a first machine learning algorithm to train a model to determine a plurality of nutritional needs for a user. A second machine learning process may be trained with a variety of available resources to determine the accuracy of user-reported nutritional intake data. User-reported nutritional intake data may be input into a machine learning process including a model trained with this data to determine a user nutritional input. A machine learning process may calculate a nutritional deficiency based on a nutritional input and a nutritional need. A machine learning process may determine an appropriate supplement plan based on at least a nutritional deficiency. Supplement plan may include supplement regimen, including in non-limiting examples supplement dosage, frequency of use, and how supplement address deficiency.

Figure 1:
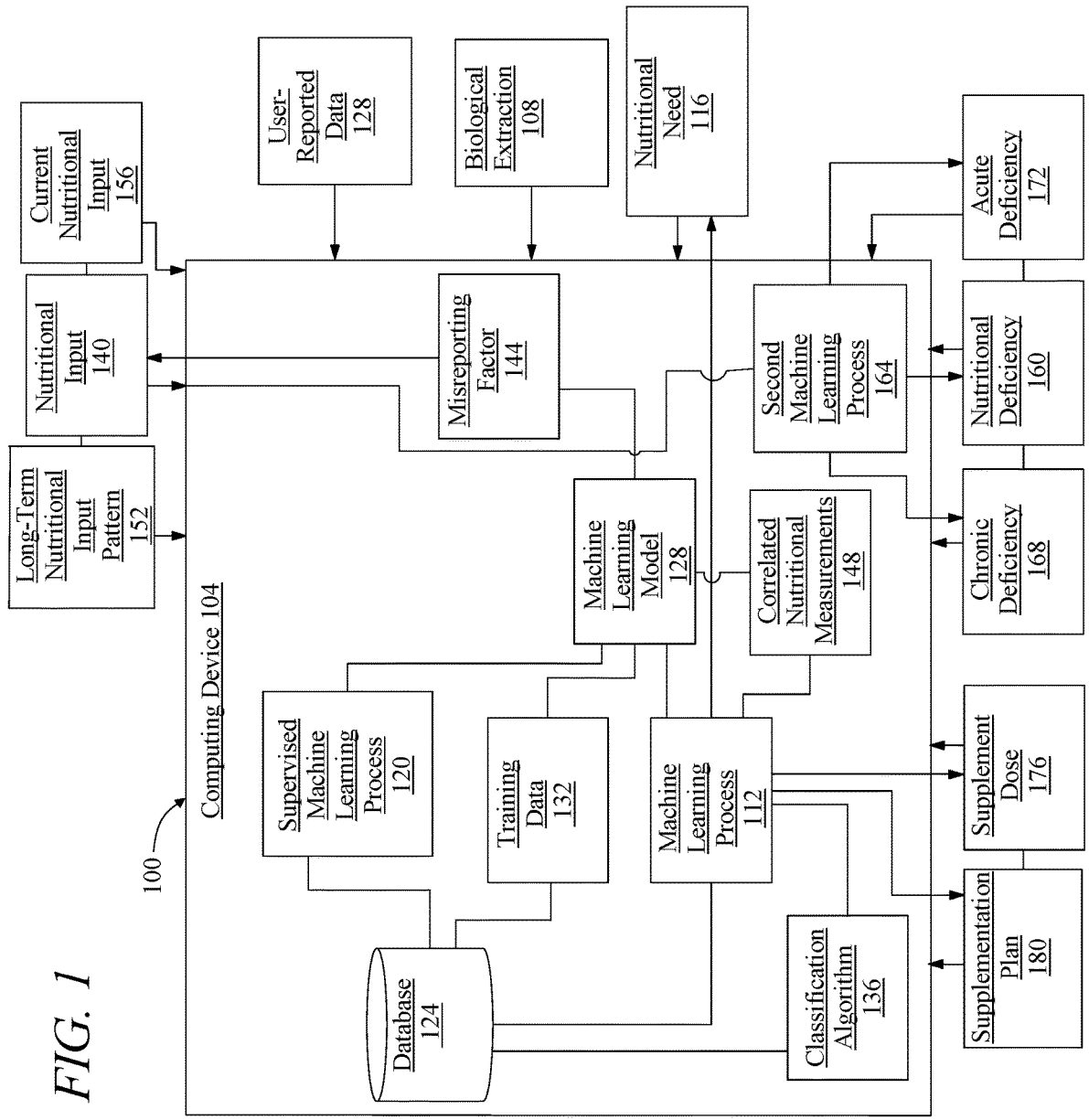
FIG. 1 is a block diagram of an exemplary embodiment of a system for determining nutritional needs to generate a supplementation plan.

Referring now to FIG. 1, an exemplary embodiment of a system 100 for determining nutritional needs using artificial intelligence is illustrated. System 100 includes at least a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently, or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may be designed and configured to receive at least a biological extraction 108. A "biological extraction," as used in this disclosure may refer to any biomarker, genetic or epigenetic indication, microbiome, or any chemical, biological, or physiological markers of data of a user, including for instance, and without limitation, as described in U.S. Nonprovisional application Ser. No. 16/865,740, filed on May 4, 2020, and entitled "METHODS AND SYSTEMS FOR SYSTEM FOR NUTRITIONAL RECOMMENDATION USING ARTIFICIAL INTELLIGENCE ANALYSIS FOR IMMUNE IMPACTS," the entirety of which is incorporated herein by reference.

Still referring to FIG. 1, at least a computing device 104 may generate, using the at least a biological extraction 108 and a first machine learning process 112, a plurality of nutritional needs 116 of the user. As used in this disclosure, a "nutritional need," refers to a quantity of at least a nutrient and/or of a plurality of nutrients that is recommended for health of user. Nutrient may refer to, without limitation, macronutrients, such as protein, including non-essential amino acids, essential amino acids, fats including non-essential fats, essential fats such as long-chain polyunsaturated fatty acids (LC-PUFAs), short-chain polyunsaturated fatty acids (SC-PUFAs), omega fatty acids, carbohydrates, including digestible and non-digestible carbohydrates such as dietary fiber, inulin, psyllium, and methylcellulose; micronutrients, such as vitamin A, thiamin (vitamin B1), riboflavin (vitamin B2), niacin (vitamin B3), pantothenic acid (vitamin B5), vitamin B6, biotin (vitamin B7), folate (vitamin B12), vitamin C, vitamin D2, vitamin D3, vitamin E, vitamin K1, vitamin K2; minerals such as calcium, phosphorous, potassium, sodium, magnesium; trace elements such as iron, sulfur, manganese, selenium, chromium, molybdenum, copper, cobalt; halides such a chloride and iodine; electrolytes and salts including bicarbonate, creatine, and phosphocreatine; caloric content, or any other substance that provides nourishment essential for growth and maintenance of a user. A "machine-learning process," as used in this disclosure, is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language may be implement using, for instance, any supervised machine learning algorithm.

Still referring to FIG. 1, machine learning process 112 may use at least a supervised machine learning algorithm. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include an element of biological extraction 108 data as described above as inputs, nutritional needs 116 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

Supervised machine learning processes may include classification algorithms, defined as processes whereby at least a computing device 104 derives, from training data, a model for sorting inputs into categories or bins of data. Classification may be performed using, without limitation, linear classifiers such as without limitation logistic regression and/or naive Bayes classifiers, regression algorithms, nearest neighbor classifiers, support vector machines, decision trees, boosted trees, random forest classifiers, and/or neural network-based classifiers, such as supervised neural net algorithms. Supervised machine learning processes may include, without limitation, machine learning processes as described in U.S. Nonprovisional application Ser. No. 16/520,835, filed on Jul. 3, 2019, and entitled "METHODS AND SYSTEMS FOR ACHIEVING VIBRANT CONSTITUTION BASED ON USER INPUTS," the entirety of which is incorporated herein by reference.

Still referring to FIG. 1, computing device 104 may select at least a machine learning process 112 and/or supervised machine learning process 120, as described before, and the at least an element of biological extraction 108 data to generate an output that is at least a nutritional need 116 of a user of a plurality of nutritional needs 116. Machine learning process 112, and/or a machine learning model 124 produced thereby, may be trained by at least a computing device using training data, which may be retrieved from a database 128, as described below, as it correlates to user biological extraction 108 data. Machine learning process 112 may accomplish this by using user-reported data 132 as it relates to at least a biological extraction 108 and a calculated nutrition value as it relates to other users.

Continuing in reference to FIG. 1, "training data," as used herein, is data containing correlations that a machine learning process 112 may use to model relationships between two or more categories of data elements. For instance, and without limitation, training data 136 may include a plurality of data entries, each entry representing a set of data elements that were recorded, received, and/or generated together; data elements may be correlated by shared existence in a given data entry, by proximity in a given data entry, or the like. Multiple data entries in training data 136 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 136 according to various correlations; correlations may indicate causative and/or predictive links between categories of data elements, which may be modeled as relationships such as mathematical relationships by machine learning processes as described in further detail below. Training data 136 may be formatted and/or organized by categories of data elements, for instance by associating data elements with one or more descriptors corresponding to categories of data elements. As a non-limiting example, training data 136 may include data entered in standardized forms by persons or processes, such that entry of a given data element in a given field in a form may be mapped to one or more descriptors of categories. Elements in training data 136 may be linked to descriptors of categories by tags, tokens, or other data elements; for instance, and without limitation, training data 136 may be provided in fixed-length formats, formats linking positions of data to categories such as comma-separated value (CSV) formats and/or self-describing formats such as extensible markup language (XML), enabling processes or devices to detect categories of data.

Alternatively or additionally, training data 136 may include one or more elements that are not categorized; that is, training data 136 may not be formatted or contain descriptors for some elements of data. Machine learning algorithms and/or other processes may sort training data 136 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 136 to be made applicable for two or more distinct machine learning algorithms as described in further detail below. Training data 136 used by computing device 104 may correlate any input data as described in this disclosure to any output data as described in this disclosure. As a non-limiting illustrative example, at least an element of biological extraction 108 data and nutritional needs 116 of a user might be used with invention Referring now to FIG. 2, a non-limiting exemplary embodiment of a database 128 is illustrated. Database 128 may refer to a "nutrition database 200" which at least a computing device 104 may, alternatively or additionally, store and/or retrieve data from a nutritional need table 204, nutritional input table 208, and nutritional deficiency table 212. Determinations by a machine learning process 112 may also be stored and/or retrieved from the nutrition database 200, for instance in non-limiting examples a misreporting factor. As a non-limiting example, nutrition database 200 may organize data according to one or more nutrition database 200 tables. One or more database tables may be linked to one another by, for instance in a non-limiting example, common column values. For instance, a common column between two tables of database 128 may include an identifier of a submission, such as a form entry, textual submission, research paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which data from one or more tables may be linked and/or related to data in one or more other tables.

Figure 2:
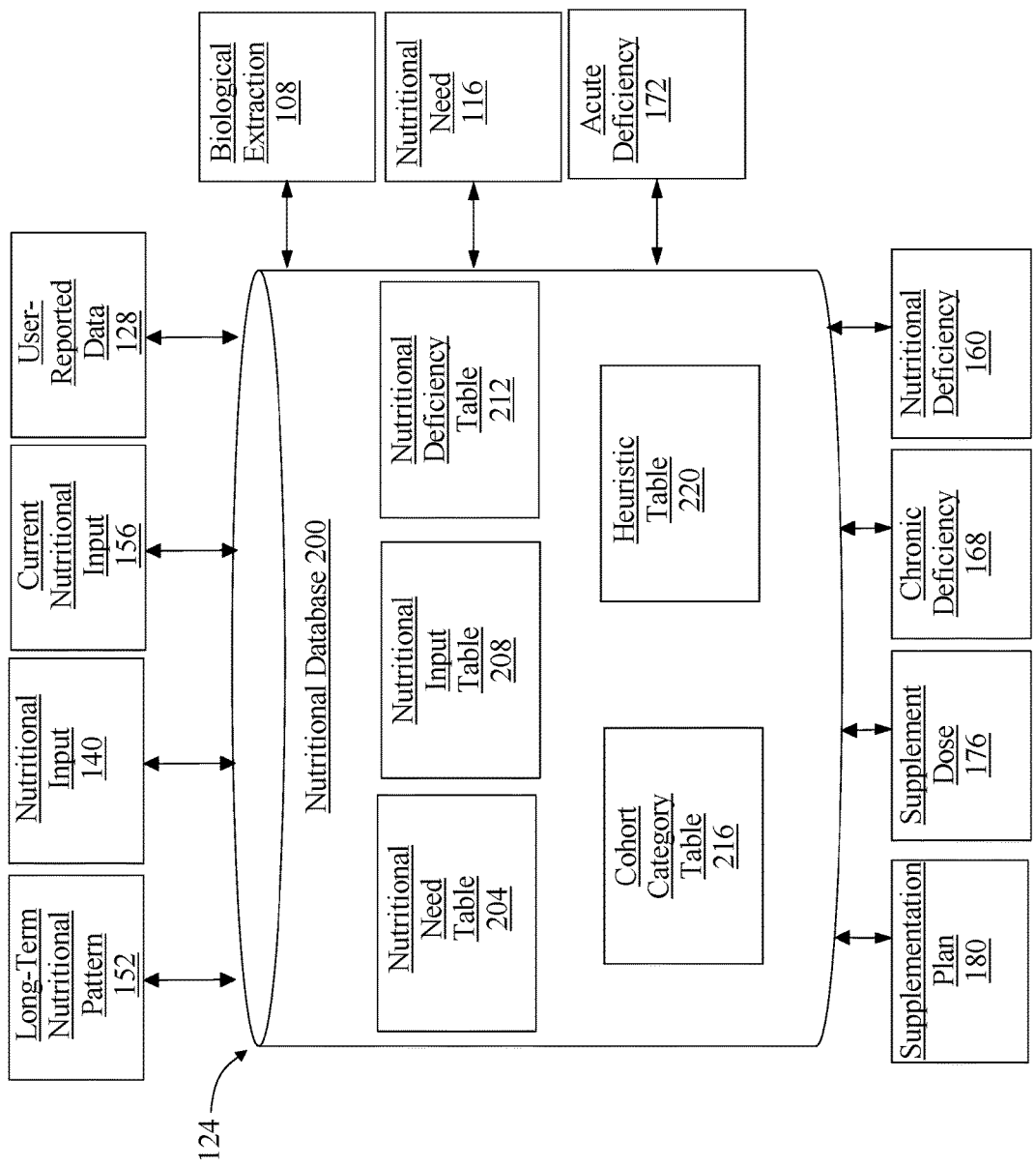
FIG. 2 is a block diagram of an exemplary embodiment of a database.

Still referring to FIG. 2, in a non-limiting embodiment, one or more nutritional database tables of a database 128 may include, as a non-limiting example, a nutritional need table 204, which may include nutritional need recommendations for use in predicting nutritional need of a user and/or correlating biological extraction 108 data, entries indicating degrees of relevance to and/or efficacy in predicting nutritional needs 116 of a user, and/or other elements of data computing device 104 and/or system 100 may use to determine usefulness and/or relevance of biological extraction 108 in determining nutritional need 112 as described in this disclosure. One or more tables may include a nutritional need table 204, which may correlate biological extraction 108 data and/or combinations thereof to one or more measures of nutritional need 112; nutritional need table 204 may contain a plurality of entries associating at least an element of biological extraction 108 data with nutritional need 112. One or more tables may include, without limitation, a nutritional input table 208 which may contain one or more inputs identifying one or more categories of data, for instance user-reported meals. One or more tables may include, without limitation, a nutritional deficiency table 212, which may contain one or more inputs identifying one or more categories of data, for instance previous user nutrient deficiencies. One or more tables may include, without limitation, a cohort table 216 which may contain one or more inputs identifying one or more categories of data, for instance demographic data, medical history data, physiological data, or the like, with regard to which users having matching or similar data may be expected to have similar nutritional needs 116 and/or nutritional deficiencies as a result of nutritional input elements and/or other biological extraction 108 data. One or more tables may include, without limitation, a heuristic table 220, which may include one or more inputs describing potential mathematical relationships between at least an element of biological extraction 108 data and nutritional needs 116, as described in further detail below.

As a non-limiting example, and referring again to FIG. 1, detecting a correlation of at least an element of biological extraction 108 data to at least a nutritional need 116, for instance and without limitation using machine-learning process 112, may include detecting an effect of at least an element of biological extraction 108 on at least a nutritional need 116. Computing device 104 may select at least an element of biological extraction 108 data to which a correlation may be determined; without limitation, selected at least an element of biological extraction 108 data may be transmitted to user and/or a person, entity, and/or device performing a correlation. Alternatively or additionally, existing data, test, or results, for instance, in a database 128 and/or otherwise available to computing device 104 may be retrieved according to selection of at least an element of biological extraction 108. Selection of at least an element of biological extraction 108 may be performed according to a score or other quantitative datum indicating a degree of impact and/or effect on nutritional need 112 and/or association therewith; in other words, quantitative datum and/or score may indicate a degree to which a given measurement and/or level of a given biological extraction 108 may be correlative with a degree of efficacy and/or accuracy of a nutritional need. At least an element of biological extraction 108 may be selected where quantitative datum and/or score correlates to a value. Any value, quantitative datum, and/or score may be provided by one or more inputs, which may be received directly from submissions via user interface forms or the like, and/or retrieved from a database 128 recording such submissions. In non-limiting examples, a computing device 104 may be configured to support a user interface form which may include a graphical user interface for data input. Graphical user interface may receive data from a user, for instance, by prompting a user to input data that can be collected and organized by a computing device 104. It will be understood by those skilled in the art, after reviewing the disclosure in its entirety, the various ways data may be input in a computing device 104 by a user. Any value, quantitative datum, and/or score may be acquired, for instance in a non-limiting example, from an online source, database 128, repository, or any other place where data may be available including without limitation, PubMed, National Institutes of Health (NIH), National Science Foundation (NSF), National Academies of Science, Engineering and Medicine, clinical trials, research journals, periodicals, presentations, seminars, studies, trials, medical devices, experiments, or any other source of biological extraction 108 data. Data may be classified to like users, or subsets of users, and training data 136 could be limited to such subsets using a classifier or other identifying means. User classifier may be used to train a machine learning process 112 and/or a supervised machine learning process 120. Classifier may distinguish a commonality or relationship among users based on, for instance in non-limiting examples, biological extraction 108 and how it relates to a nutrition need. A machine learning process 112 could be trained on a dataset limited to the subset of biological extraction 108 data and its relationship to a nutrition need.

Continuing in reference to FIG. 1, a user and such human subjects may be matched to one another using a classifier identifying them as mutually similar with respect to the one or more categories of data described herein. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. User classifier may be configured to output identifiers of a bin and/or set of users identified as similar using classification algorithm 140, where a "identifier" is a datum that labels or otherwise identifies a user set; that is, a label identifying a set of users that have sets of user data, such as without limitation biological extractions, that are clustered together, found to be close under a distance metric as described below, or the like. A user set may be a collection of users having closely related user data regarding one or more categories for classification as described above. User classifier may include a classifier configured to input user data and output user set identifiers.

Further referring to FIG. 1, computing device 104 and/or another device may generate user classifier using a classification algorithm 140, defined as a process whereby a computing device 104 derives a classifier from user classification training data 136. User classifier may be trained by computing device 104 and/or one or more other devices in or communicating with system 100 using training data 136 containing a plurality of sets of data pertaining to a plurality of persons. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Continuing in reference to FIG. 1, a classifier may indicate a subset of users mutually similar in at least one or more elements of data including biological extraction 108 data, user-reported data 132, nutritional needs 116, nutritional inputs, nutritional deficiencies, supplement plan, and/or any other available data, to match a user to a nutritional standard. Matching a user to a nutritional standard via a classifier or subset of users may correspond to identifying any mathematical, correlational, proportional, and/or any other relationship between a user's biological extraction 108, nutritional needs 116, nutritional inputs, nutritional deficiencies, and/or supplement plan, and other users. A classifier may be an input to a machine learning process 112 to calculate, modify, or otherwise generate nutritional needs 116, nutritional inputs, nutritional deficiencies, and/or supplement plan information for a user. Classifiers generated from a classification algorithm 140 may be stored and/or retrieved in a database 128, such as a nutritional database, for use by machine learning process 112, as described herein, including for instance, and without limitation, as described in U.S. Nonprovisional application Ser. No. 16/865,740, filed on May 4, 2020, and entitled "METHODS AND SYSTEMS FOR SYSTEM FOR NUTRITIONAL RECOMMENDATION 140 USING ARTIFICIAL INTELLIGENCE ANALYSIS FOR IMMUNE IMPACTS," the entirety of which is incorporated herein by reference.

Still referring to FIG. 1, computing device 104 may be configured to generate user classifier 128 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate user classifier 128 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute 1 as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including a plurality of user data to vectors representing similar users' data.

Still referring to FIG. 1, computing device 104 may be configured to determine nutritional input 144 for user by inferring nutritional input 144, using a machine-learning process, from the at least a biological extraction 108. In a non-limiting example, nutritional input 144 may be determined by at least a computing device 104 from, for instance, user-reported data 132, user-reported data 132 and a value determined from a database 128, user-reported data 132 and at least an element of biological extraction 108, or any combination thereof. As used in this disclosure, "user-reported data" is any nutritional input 144 information, for instance and without limitation, a meal consumed, provided to a computing device 104 from a user. In non-limiting examples, a computing device 104 may receive user-reported data 132 and/or biological extraction 108 data via a graphical user interface, as previously described. A machine-learning process may infer the nutritional inputs 140 from user-reported data 132, for instance in non-limiting examples, from user-reported meals mapped to nutrient amounts. Machine learning process 112 may be able to retrieve information from a nutrition database 200, or other source, to determine nutrient values for a user-reported meal to determine the nutritional input 144 of the user. In non-limiting examples, a machine learning process 112 may take nutritional values, for instance as determined in the previously described ways, as an input and use at least a biological extraction 108 to determine the nutritional input 144 for the user, for instance, by taking into account a metabolic disorder or digestive difficulty.

Continuing in referring to FIG. 1, a system 100 determining a nutritional input 144 for the user includes receiving user-reported data 132 describing the nutritional input 144. A computing device 104 may be configured to determine a nutritional input 144 from at least a user-reported datum 136 of a plurality of user-reported data 132 describing nutritional input 144. As used in this disclosure, a "nutritional input" is a nutritional intake of a user as it relates to any of the categories or values represented by a nutritional need, as described previously. Nutritional input 144 refers to at least a value of a nutrient of a plurality of values of nutrients, determined as described herein, which describe an amount of a nutrient from user-reported nutritional intake data. User-reported nutritional intake data may be, for instance without limitation, meals or food items mapped to nutrition inputs. Mapping user-reported nutritional intake may be performed by a machine learning process 112 or may be mapped using database 128 entries, as described before. Alternatively or additionally, mapping user-reported nutritional intake may be performed by a machine learning model 124 trained with data described herein. Mapping user-reported nutritional intake to determine a nutritional input 144 may, for instance and without limitation, include determining an amount of a vitamin that was consumed from a user-reported meal.

Continuing in referring to FIG. 1, alternatively or additionally, a computing device 104 configured to calculate a user misreporting factor 148 and weighting the user-reported data 132 with the misreporting factor 148. A "user misreporting factor," as used herein, is a numerical quantity representing a probability or degree of likelihood that a user is over or under-reporting a user-reported nutritional input. A machine learning process 112, such as without limitation a supervised machine learning process 120 may be implemented, as described above, to calculate a user misreporting factor 148. User misreporting factor 148 can be used to weight user-reported data 132 to generate a nutrition input 140. A machine learning algorithm may be trained with data retrieved from an available source, for instance from a nutrition database 200 as described herein, including for instance in non-limiting examples data on user nutrient absorption, nutrient pharmacokinetics, digestive disorders, accuracy of nutrition labels, portion sizes, or any data as it relates to the reporting of nutrient intake. In non-limiting examples, a machine learning model 124 may be trained with this data to detect for instance any mathematical, correlational, or other relationship between user nutrition intake and reporting of user nutrition intake, any tendency to underestimate and/or overestimate nutritional intake. A machine learning model 124 may be trained in this manner to calculate at least a user misreporting factor 148 of a plurality of misreporting factors 144. A machine learning process 112 may use a model trained in the above described manner and user-reported nutrition intake as inputs to calculate a misreporting factor 148-weighed nutrition input as a generated output. In non-limiting illustrative embodiments, a machine learning model 124 trained for at least a user misreporting factor 148, may weight, adjust, correct, or otherwise modify user-reported data 132 as it relates to nutritional input 144 to result in more accurate nutritional intake reporting than user-reported data 132 alone.

With continued reference to FIG. 1, computing device 104 is configured to determine a nutritional input to a user, wherein determining the nutritional input to the user comprises receiving user-reported data describing a nutritional input, calculating a user misreporting factor, and weighting the user-reported data with the user misreporting factor. This may be performed utilizing any of the methodologies as described herein. Computing device 104 is configured to determine a nutritional input by generating a first machine-learning model, wherein the first machine-learning model utilizes a biological extraction as an input and outputs a nutritional input. First machine-learning model may be implemented as any machine-learning model as described herein. First machine-learning model is trained using training data including a plurality of biological extractions and a plurality of correlated nutritional inputs.

Continuing in referring to FIG. 1, calculating a misreporting factor 148 further comprises using a machine learning process 112, wherein the machine learning process 112 is trained using training data 136 including a plurality of past user inputs and a plurality of correlated nutritional measurements 152. A plurality of past user inputs, as described herein may include any user-reported data 132 regarding nutritional intake, for instance in non-limiting examples, a food item or meal. A machine learning process 112 may be trained as previously described may generate a machine learning model 124 with correlated nutritional measurements 152, as described herein, between past user-reported nutritional inputs 140 and the current user-reporting. In non-limiting examples machine learning process 112 data, including for instance any models and/or outputs generated from user-reported data 132, misreporting factors 144, and/or nutritional inputs 140 may be stored in a database 128 for training subsequent machine learning models 124, as illustrated in FIG. 2. A machine learning process 112 may be a supervised learning process, as described herein.

Continuing in referring to FIG. 1, a system 100 determining a nutritional input 144 for the user includes determining a long-term nutritional input pattern 156. As used herein, "long-term nutritional input pattern" is an element of data describing a consistent rate of consumption and/or a regular quantity consumed, of a nutrient; a long-term nutritional input pattern 156 may include, without limitation, user-reported nutritional input 144 data from days, weeks, months, years, or any amount of time. A machine learning process 112 may determine a long-term nutritional input pattern 156 using a machine learning model 124 trained with at least a correlated nutritional measurement 148 and at least a past user-reported input of a plurality of past user-reported nutritional input 144 to determine a long-term nutritional input pattern 156. A long-term nutritional input pattern 156 and any associated data may be stored and/or retrieved from a database 128 for use by further machine learning processes. In non-limiting illustrative examples, a machine learning process 112 may extract months of user-reported nutritional intake data from a database 128 to generate a long-term nutritional input pattern 156. In non-limiting illustrative examples, a long-term nutritional input pattern 156 may include months of user-reported nutritional intake data weighed with a misreporting factor 148 calculated from months of user-reported nutritional intake.

Continuing in reference to FIG. 1, a system 100 determining a nutritional input 144 for a user includes determining a current nutritional input 160. As described in this disclosure, a "current nutritional input," is a nutritional input 144 generated from a most recent user-reported nutritional intake or set of intakes, including for instance in non-limiting examples, over a recent period of time such as a day, week, or the like. Alternatively or additionally, a machine learning process 112 and/or model may use any correlated nutritional measurements 152 or other available information, such as a misreporting factor 148, to generate a current nutritional input 160. In non-limiting examples, a machine learning process 112 may retrieve prior machine learning models 124 and/or outputs, for instance from a nutrition database 200, to generate a current nutritional input 160. In non-limiting embodiments, a machine learning model 124 may be trained with at least an element of biological extraction 108 and/or a long-term nutritional input pattern 156 to generate a model that weights, corrects, or otherwise adjusts user-reported current notational input data. Models trained in this way, as described above, may determine correlated nutritional measurements 152 such as nutrition values, misreporting factors 144, or any other data related to the calculation of a current nutritional input 160 to weight, adjust, correct, or otherwise modify user-reported nutritional intake data, such as a meal recently consumed. This may include, for instance and without limitation user-reported nutritional input 144 as it is being input into a system 100 in real-time. A machine learning model 124 may be trained, as described above, with at least a first element of biological extraction 108 data and/or at least a most recent user-reported nutrition intake input to determine any correlated nutritional measurements 152 or other relationships in the data. In non-limiting examples, a machine learning process 112 may use a model trained in such a manner and a most recent user-reported input to output a current nutritional input 160.

Continuing in reference to FIG. 1, computing device is configured to detect a nutrition deficiency. As described herein, "nutritional deficiency," is a calculated value that corresponds to any deficit in a nutrient value between a nutritional need and a nutritional input 144. As a non-limiting example, detecting a nutrition deficiency may include calculating the deficiency using a second machine learning process 168, that inputs the at least a nutritional input 144 and outputs a nutritional deficiency 164. A computing device 104 may be configured to support second machine learning process 168 which may use a nutritional input 144, as described before, as an input to calculate a nutritional deficiency 164 of a user, for instance in non-limiting examples, by calculating a difference between a nutritional input 144 and a nutritional need generating an output value of a plurality of output values. Alternatively or additionally, a second machine learning process 168 may use a model trained, as described above, with at least an element of biological extraction 108 data and/or user-reported data 132 to calculate a nutritional deficiency 164. Second machine learning process 168 may include supervised machine learning process 120. Second machine learning process 168 may calculate a nutrient deficiency using a nutrient input and data retrieved and/or stored on a nutrition database 200. In non-limiting examples, a nutritional deficiency 164 may be calculated by subtracting a nutritional input 144 of a nutrient from a nutritional need of the same nutrient to determine if a deficiency exists.

Continuing in reference to FIG. 1, a system 100 detecting a nutrition deficiency of a user includes detecting a chronic deficiency 172. A computing device 104 may be configured to detect a chronic deficiency 172 by using a machine learning process 112, as described before. A machine learning process 112 may be a supervised machine learning process 120. A "chronic deficiency," as used in this disclosure, is a nutritional deficiency 164 that is present over a long period, or as a persistent pattern. A chronic deficiency 172 may be detected using a long-term nutritional input pattern 156 of a plurality of long-term nutritional input patterns 156 and/or long-term user-reported nutritional intake that indicate a nutritional deficiency 164 is not due to a current nutritional intake deficiency. In non-limiting examples, at least an element of biological extraction 108 may be an input used by a machine learning process 112 to detect a chronic deficiency 168, for example, blood glucose data as it relates to carbohydrate intake.

Continuing in reference to FIG. 1, a system 100 detecting a nutrition deficiency of a user include detecting an acute deficiency 176. A computing device 104 may be configured to detect an acute deficiency 176 by using a machine learning process 112, as described before. A machine learning process 112 may be a supervised machine learning process 120. An "acute deficiency," as described herein refers to a nutritional deficiency 164 that is present in current user-reported nutrition input, or as a current pattern. An acute deficiency 176 may be detected using a current nutritional input 160 of a plurality of current nutritional inputs 156 and/or most recent user-reported nutritional intake that indicate a nutritional deficiency 164 is not due to a long-term nutritional intake deficiency and/or long-term nutritional input pattern 156. In non-limiting examples, at least an element of biological extraction 108 may be an input used by a machine learning process 112 to detect a chronic deficiency 168, for example, diabetes as it relates to per-meal carbohydrate intake. A machine learning process 112 may determine the difference between a chronic and acute nutritional deficiency 164 and may adjust a supplement dose based on this information.

Continuing in referring to FIG. 1, a supplement dose 180 includes a plurality of supplements combined to address a plurality of nutrient deficiencies. A computing device 104 configured to support a machine learning process 112 may calculate at least a supplement dose 180 of a plurality of supplements from the plurality of nutritional needs 116 and at least a nutritional deficiency 164 of a plurality of nutritional deficiencies. A machine learning process 112 may be a supervised machine learning process 120, as described above. A "supplement dose," as used in this disclosure, is an amount of a supplement intended to address a deficiency. In non-limiting examples, a supplement dose 180 may be a calculated value mapped to a nutrient deficiency, wherein without limitation, a supplement value may be a mass amount of a supplement that address a nutrient deficiency by making up the difference required to reach a nutritional need. A machine learning process 112 may use a nutritional need of a plurality of nutritional needs 116, determined as described before, and/or at least a nutritional deficiency 164, calculated as described before, as inputs to generate an output of at least a supplement dose 180 of a plurality of supplements. A machine learning process 112 may use a model trained with at least an element of biological data to generate a supplement dose 180 of a plurality of supplements to address a plurality of nutrient deficiencies. In non-limiting examples, outputs of supplement doses 180 of the plurality of supplements may be stored and/or retrieved from a nutritional database as training data 136 for further machine learning processes. In non-limiting examples, a machine learning process 112 may train a model with prior supplement dose 180 outputs of a plurality of supplements to calculate subsequent supplement doses 180.

Continuing in referring for FIG. 1, computing device 104 may be configured to generate a nutrient supplementation plan 184; generation may include calculating at least a supplement dose 180 from the plurality of nutritional needs 116 and the least a nutrition deficiency. Supplementation plan 184 may be calculated by a computing device 104 configured to support a machine learning process 112. A machine learning process 112 may be a supervised machine learning process 120. A supplement plan 180 may comprise a supplement regimen, wherein a supplement regimen may refer to a supplement dose 180 and frequency of use of a plurality of supplements. Supplement regimen may be an instantaneous dose, that is calculated as a single measured dosage for a user such as an amount of mass of a vitamin per amount of mass bodyweight, or a supplement regimen may be a calculated dosage that deviates from this instantaneous dose, for instance in non-limiting examples an amount of mass of a vitamin per amount of mass bodyweight that is taken daily over the span of a month, decreasing in amount each week. Supplement regimen may be any combination of at least an instantaneous dose and at least a second dose of one or more supplements. Supplement plan 180 may include an output of a calculated value of an amount of a supplement and how it addresses at least a nutritional deficiency 164 and/or nutritional need. In non-limiting examples, supplement plan 180 may be determined by a machine learning process 112 that calculates a supplement plan 180 based on input data, for instance, biological extraction 108 data, user-reported data 132, nutritional need data, nutritional input 144 data, nutritional deficiency 164 data, or any other available data to provide an output corresponding to at least a compatible supplement, a supplement dosage, a user supplement frequency, information on combining a plurality of supplements, and/or how a supplement addresses a deficiency. A machine learning process 112 for calculating, or otherwise adjusting, supplement plan 180 outputs may make use of an algorithm or model trained with data described above. Supplement plan 180 may be determined based on data that corresponds to supplement plan 180 outputs of other users or subsets of users that match user classifiers or other identifiers. Supplement plan 180 outputs may be stored and/or retrieved from a nutritional database to train machine learning models 124, as described above.

Continuing in reference to FIG. 1, determining a supplement plan 180 may include performing a machine learning process 112, with user-reported data 132 after a first supplement plan 180 has been recommended as an input, to determine how a user responds to a supplement dosage over time. A computing device 104 and/or machine learning process 112 may use an input that is user-reported data 132 and/or biological extraction 108 data after a supplement plan 180 has been adopted by a user to identify how a user responds to a supplement plan 180. Machine learning process 112 may be trained, as previously described, with data that corresponds to how a user responds to a supplement plan 180. Machine learning process 112 trained in this way may be used to inform subsequent supplement plans 180. These outputs and/or machine learning algorithms and/or models generated from training a machine learning process 112 in this way may represent data that can be used to identify classifiers, or subsets of users, based on how a user responds to a supplement plan 180. Outputs generated in this manner may be stored and/or retrieved from a database 128, as described above.

Figure 3:
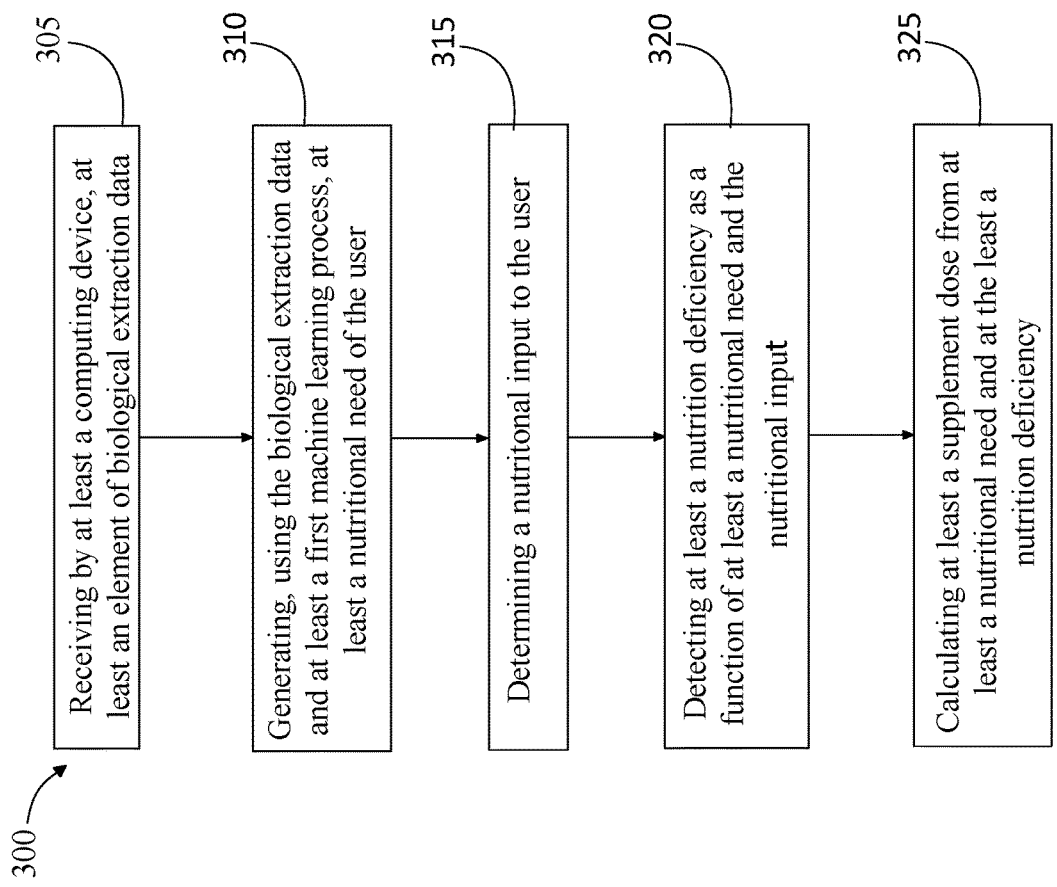
FIG. 3 is a flowchart describing a method using the system of the invention.

Referring now to FIG. 3, an exemplary embodiment of a method 300 of calculating at least a supplement dose 180 using an element of user data and artificial intelligence is illustrated. At step 305 at least a computing device 104 receives at least an element biological extraction 108; this may be performed, without limitation, as described above in reference to FIGS. 1-2. At step 310, a computing device 104 generates at least a nutritional need as an output from biological extraction 108 data and a machine learning process 112; this may be implemented, without limitation, as described above in reference to FIGS. 1-2. It will be understood by those skilled in the art, after reviewing the disclosure in its entirety, the various ways data may be input in a computing device 104 by a user. At step 315, a computing device 104 determines a nutritional input 144 to the user using a machine learning process 112; this may be implemented, without limitation, as described above in reference to FIGS. 1-2. Determining a nutritional input includes receiving user-reported data describing a nutritional input, calculating a user misreporting factor, and weighting the user-reported data with the user misreporting factor. Determining a nutritional input includes generating a first machine-learning model, which may include any of the machine-learning models as described herein. First machine-learning model utilizes a biological extraction as an input and outputs a nutritional input. First machine-learning model is trained using training data It will be understood by those skilled in the art, after reviewing the disclosure in its entirety, the various ways outputs may be displayed by a computing device 104 to a user. At step 320, a computing device 104 may detect at least a nutrition deficiency as a function of at least a nutritional need and the nutritional input 144, as described herein; this may be implemented, without limitation, as described above in reference to FIGS. 1-2. At step 325, a computing device 104 may calculate at least a supplement dose 180 from at least a nutritional need and at least a nutritional deficiency 164; this may be implemented, without limitation, as described above in reference to FIGS. 1-2. It will be understood by those skilled in the art, after reviewing the disclosure in its entirety, the various ways data may be input in a computing device 104 and the various ways outputs may be displayed by a computing device 104 to a user for all steps described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 4:
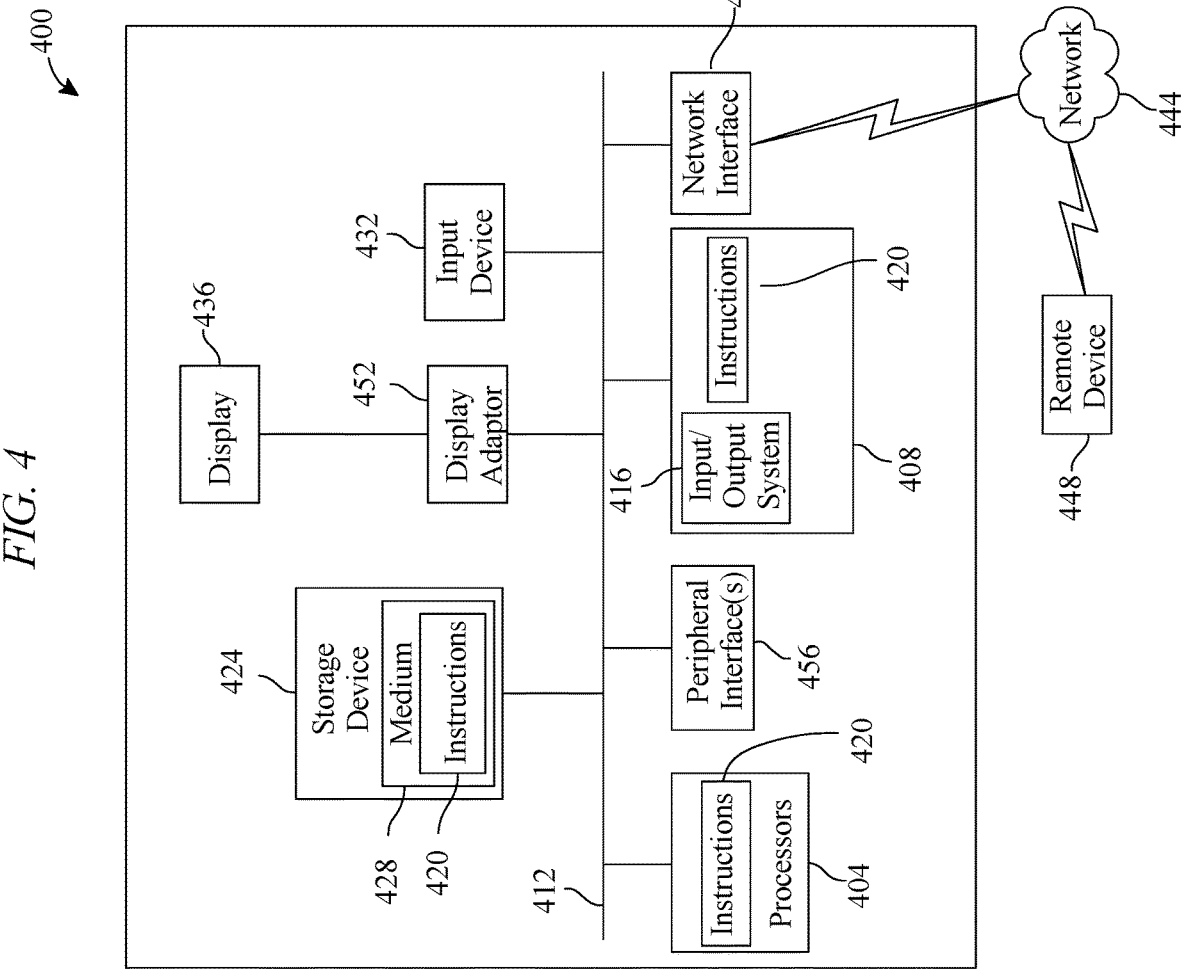
FIG. 4 is a block diagram of a computing system that can be used to implement any one or more of the methodologies disclosed herein and any one or more portions thereof.

FIG. 4 shows a diagrammatic representation of one embodiment of a computing device in the exemplary form of a computer system 400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 400 includes a processor 404 and a memory 408 that communicate with each other, and with other components, via a bus 412. Bus 412 may include any of several types of bus structures including, but not limited to, a memory bus, a memory controller, a peripheral bus, a local bus, and any combinations thereof, using any of a variety of bus architectures.

Processor 404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 404 may be organized according to Von Neumann and/or Harvard architecture as a non-limiting example. Processor 404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 408 may include various components (e.g., machine-readable media) including, but not limited to, a random-access memory component, a read only component, and any combinations thereof. In one example, a basic input/output system 416 (BIOS), including basic routines that help to transfer information between elements within computer system 400, such as during start-up, may be stored in memory 408. Memory 408 may also include (e.g., stored on one or more machine-readable media) instructions (e.g., software) 420 embodying any one or more of the aspects and/or methodologies of the present disclosure. In another example, memory 408 may further include any number of program modules including, but not limited to, an operating system, one or more application programs, other program modules, program data, and any combinations thereof.

Computer system 400 may also include a storage device 424. Examples of a storage device (e.g., storage device 424) include, but are not limited to, a hard disk drive, a magnetic disk drive, an optical disc drive in combination with an optical medium, a solid-state memory device, and any combinations thereof. Storage device 424 may be connected to bus 412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 424 (or one or more components thereof) may be removably interfaced with computer system 400 (e.g., via an external port connector (not shown)). Particularly, storage device 424 and an associated machine-readable medium 428 may provide nonvolatile and/or volatile storage of machine-readable instructions, data structures, program modules, and/or other data for computer system 400. In one example, software 420 may reside, completely or partially, within machine-readable medium 428. In another example, software 420 may reside, completely or partially, within processor 404.

Computer system 400 may also include an input device 432. In one example, a user of computer system 400 may enter commands and/or other information into computer system 400 via input device 432. Examples of an input device 432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 432 may be interfaced to bus 412 via any of a variety of interfaces (not shown) including, but not limited to, a serial interface, a parallel interface, a game port, a USB interface, a FIRE-WIRE interface, a direct interface to bus 412, and any combinations thereof. Input device 432 may include a touch screen interface that may be a part of or separate from display 436, discussed further below. Input device 432 may be utilized as a user selection device for selecting one or more graphical representations in a graphical interface as described above.

A user may also input commands and/or other information to computer system 400 via storage device 424 (e.g., a removable disk drive, a flash drive, etc.) and/or network interface device 440. A network interface device, such as network interface device 440, may be utilized for connecting computer system 400 to one or more of a variety of networks, such as network 444, and one or more remote devices 448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 444, may employ a wired and/or a wireless mode of communication. In general, any network topology may be used. Information (e.g., data, software 420, etc.) may be communicated to and/or from computer system 400 via network interface device 440.

Computer system 400 may further include a video display adapter 452 for communicating a displayable image to a display device, such as display device 436. Examples of a display device include, but are not limited to, a liquid crystal display (LCD), a cathode ray tube (CRT), a plasma display, a light emitting diode (LED) display, and any combinations thereof. Display adapter 452 and display device 436 may be utilized in combination with processor 404 to provide graphical representations of aspects of the present disclosure. In addition to a display device, computer system 400 may include one or more other peripheral output devices including, but not limited to, an audio speaker, a printer, and any combinations thereof. Such peripheral output devices may be connected to bus 412 via a peripheral interface 456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for determining a plurality of nutritional needs of a user and generating a nutrient supplementation plan using artificial intelligence, the system comprising at least a computing device, wherein the computing device is designed and configured to:
   receive, from a user, at least a biological extraction;
   generate, using the at least a biological extraction and a first machine learning process, a plurality of nutritional needs of the user;
   determine a nutritional input to the user, wherein determining the nutritional input to the user comprises:
      receiving user-reported data describing the nutritional input;
      creating a first training set comprising a plurality of biological extraction data, a plurality of correlated nutritional inputs for the user, and data from a nutrition database;
      training, iteratively, a first supervised machine-learning model using a first supervised machine learning algorithm, the first training set, the at least a biological extraction, and the user-reported data describing the nutritional input;
      generating the nutritional input to the user, using the first supervised machine-learning model and a first scoring function, wherein the first scoring function represents a desired form of relationship to be detected between pairs of biological extraction datums and nutritional input datums, wherein the first supervised machine-learning model utilizes the at least a biological extraction as an input and outputs the nutritional input;
      creating a second training set comprising the at least a biological extraction, a long-term input pattern, and data from the nutrition database, the long-term input pattern comprising past reported user-report data correlated with the user-reported data;
      training, iteratively, the first supervised machine-learning model with the second training set, the at least a biological extraction, and the long-term input pattern;
      calculating a user misreporting factor, as a function of the first supervised machine-learning model, wherein the misreporting factor comprises a probability that the user is over or under-reporting the user-reported data;
      weighting the user-reported data with the user misreporting factor; and
      generating a current nutritional input as a function of the nutritional input and the weighting of the user-reported data with the user misreporting factor, wherein the current nutritional input represents an updated version of the nutritional input;
   classify a plurality of nutrition deficiencies, wherein classifying the plurality of nutrition deficiencies comprises:
      receiving the plurality of nutrition deficiencies; and
      classifying the plurality of nutrition deficiencies to a plurality of long-term input patterns related to long-term nutritional inputs;
   detect at least a nutrition deficiency, using a second supervised machine-learning model, as a function of the classification, the generated plurality of nutritional needs and the generated current nutritional input;

calculate at least a supplement dose from the generated plurality of nutritional needs and the detected at least a nutrition deficiency; and determine a response of the user to the at least a supplement dose, using the first machine learning process, as a function of the user-reported data and the at least a biological extraction.

2. The system of claim 1, wherein the computing device is configured to determine the nutritional input for the user by inferring the nutritional input, using the first supervised machine learning model, from the at least a biological extraction.

3. The system of claim 1, wherein calculating the user misreporting factor further comprises a scoring function.

4. The system of claim 1, wherein determining a nutritional input for the user further comprises determining a long-term nutritional input pattern.

5. The system of claim 1, wherein detecting a nutrition deficiency further comprises calculating the deficiency using the second machine learning model, that inputs the at least a nutritional input and outputs a nutritional deficiency.

6. The system of claim 1, wherein detecting a nutrition deficiency of a user further comprises detecting a chronic deficiency.

7. The system of claim 1, wherein detecting a nutrition deficiency of a user further comprises detecting an acute deficiency.

8. A method of calculating at least a supplement dose using at least an element of user data and artificial intelligence, the method comprising:

receiving, by at least a computing device, at least a biological extraction of a user;

generating, by the at least a computing device, using the at least a biological extraction data and a first machine learning process, at least a nutritional need of the user;

determining, by the at least a computing device, a nutritional input to the user, wherein determining the nutritional input comprises:

receiving user-reported data describing the nutritional input;

creating a first training set comprising a plurality of biological extraction data and a plurality of correlated nutritional inputs for the user;

training, iteratively, a first supervised machine-learning model using a first supervised machine learning algorithm, the first training set, the at least a biological extraction, and the user-reported data describing the nutritional input;

generating the nutritional input to the user, using the first supervised machine-learning model and a first scoring function, wherein the first scoring function represents a desired form of relationship to be detected between pairs of biological extraction datums and nutritional input datums, wherein the supervised first machine-learning model utilizes the at least a biological extraction as an input and outputs the nutritional input;

creating a second training set comprising the at least a biological extraction, a long-term input pattern, and data from the nutrition database, the long-term input pattern comprising past reported user-report data correlated with the user-reported data;

training, iteratively, the first supervised machine-learning model with the second training set, the at least a biological extraction, and the long-term input pattern;

calculating a user misreporting factor, as a function of the first supervised machine-learning model, the misreporting factor comprises a probability that the user is over or under-reporting the user-reported data;

weighting the user-reported data with the user misreporting factor; and generating a current nutritional input as a function of the nutritional input and the weighting of the user-reported data with the user misreporting factor, wherein the current nutritional input represents an updated version of the nutritional input;

classifying a plurality of nutrition deficiencies, wherein classifying the plurality of nutrition deficiencies comprises:

receiving the plurality of nutrition deficiencies; and classifying the plurality of nutrition deficiencies to a plurality of long-term input patterns related to long-term nutritional inputs;

detecting, by the at least a computing device, at least a nutrition deficiency, using a second supervised machine learning model, as a function of the classification, the generated at least a nutritional need and the generated current nutritional input;

calculating, by the at least a computing device, at least a supplement dose from the generated at least a nutritional need and the detected at least a nutrition deficiency; and determine a response of the user to the at least a supplement dose, using the first machine learning model, as a function of the user-reported data and the at least a biological extraction.

9. The method of claim 8, wherein determining the nutritional input for the user further comprises inferring the nutritional input, using the first supervised machine learning process, from the at least a biological extraction.

10. The method of claim 8, wherein calculating the user misreporting factor further comprises a scoring function.

11. The method of claim 8, wherein determining a nutritional input for the user further comprises determining a long-term nutritional input pattern.

12. The method of claim 8, wherein detecting a nutrition deficiency further comprises calculating the deficiency using the second machine learning model, that inputs the at least a biological extraction and outputs a nutritional deficiency.

13. The method of claim 8, wherein detecting a nutrition deficiency of a user further comprises detecting a chronic deficiency.

14. The method of claim 8, wherein detecting a nutrition deficiency of a user further comprises detecting an acute deficiency.

15. The system of claim 1, wherein the scoring function is an expected loss function.

16. The method of claim 8, wherein the scoring function is an expected loss function.

* * * * *